United States Patent [19]

Hough et al.

[11] Patent Number: 4,501,605

[45] Date of Patent: Feb. 26, 1985

[54] HERBICIDAL HETEROCYCLIC COMPOUNDS AND COMPOSITIONS

[75] Inventors: Thomas L. Hough, Linton; Graham P. Jones, Babraham, both of England

[73] Assignee: FBC Limited, England

[21] Appl. No.: 463,071

[22] Filed: Feb. 2, 1983

[30] Foreign Application Priority Data

Feb. 4, 1982 [GB] United Kingdom ................ 8203223

[51] Int. Cl.³ .................... C07D 285/12; A01N 43/82
[52] U.S. Cl. .......................................... 71/90; 546/140
[58] Field of Search ............................ 548/140; 71/90

[56] References Cited

U.S. PATENT DOCUMENTS 4,239,524 12/1980 Nusslein et al. ......................... 71/90

Primary Examiner—Robert Gerstl
Attorney, Agent, or Firm—Morgan, Finnegan, Pine, Foley & Lee

[57] ABSTRACT

Novel herbicidal thiadiazoles of the formula:

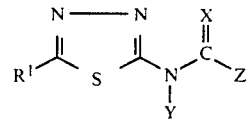

(wherein:

$R^1$ represents a group $R^a$, $-S(O)nR^a$ or $-SO_2NR^aR^b$, where $R^a$ and $R^b$, which may be the same or different, each represent hydrogen, cycloalkyl of 3 to 7 carbon atoms, alkenyl or alkynyl of 2 to 6 carbon atoms, phenyl, phenylalkyl of 7 to 10 carbon atoms, or alkyl of 1 to 10 carbon atoms, any phenyl or alkyl group present being optionally substituted by one or more halogen atoms, cyano groups, alkoxy or alkylthio groups of 1 to 4 carbon atoms, or phenoxy groups, or $R^a$ and $R^b$ together form an alkylene chain of 2 to 6 carbon atoms, and n represents 0, 1 or 2;

X represents oxygen or sulphur;

Z represents a group $-NR^cR^d$; and

Y represents a group $-NR^eR^f$ or a group $-N=CR^eR^f$; where $R^c$, $R^d$, $R^e$ and $R^f$, which may be the same or different, each represent a group as defined for $R^a$, or a carboxy, alkoxy, alkoxycarbonyl, acyl, acyloxy, alkylsulphonyl, cyano, formyl, amido or heterocyclyl group, any alkyl moiety of which is of 1 to 4 carbon atoms);

and the acid addition salts thereof, compositions containing them and processes for their preparation.

9 Claims, No Drawings

HERBICIDAL HETEROCYCLIC COMPOUNDS AND COMPOSITIONS

This invention concerns herbicidally-active thiadiazole derivatives, processes for their preparation, and compositions containing them.

In one aspect, this invention provides the thiadiazoles of the formula:

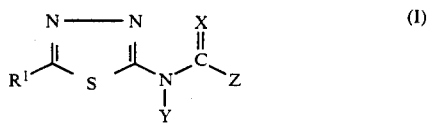

(wherein:

$R^1$ represents a group $R^a$, —S(O)n$R^a$ or —SO$_2$N-$R^aR^b$ where $R^a$ and $R^b$, which may be the same or different, each represent hydrogen, cycloalkyl of 3 to 7 carbon atoms, alkenyl or alkynyl of 2 to 6 carbon atoms, phenyl, phenylalkyl of 7 to 10 carbon atoms, or alkyl of 1 to 10 carbon atoms, any phenyl or alkyl group present being optionally substituted by one or more halogen atoms, cyano groups, alkoxy or alkylthio group of 1 to 4 carbon atoms, or phenoxy groups, or $R^a$ and $R^b$ together form an alkylene chain of 2 to 6 carbon atoms, and n represents 0, 1 or 2;

X represents oxygen or sulphur;

Z represents a group —NR$^c$R$^d$; and

Y represents a group —NR$^e$R$^f$ or a group —N=CR$^e$R$^f$; where R$^c$, R$^d$, R$^e$ and R$^f$, which may be the same or different, each represent a group as defined above for $R^a$ or a carboxy, alkoxy, alkoxycarbonyl, acyl, acyloxy, alkylsulphonyl, cyano, formyl, amido or heterocyclyl group, any alkyl moiety of which is of 1 to 4 carbon atoms), and the acid addition salts thereof.

$R^a$ preferably represents alkyl of 1 to 6, especially 1 to 4, carbon atoms, optionally substituted by one or more halogen atoms.

$R^b$ preferably represents hydrogen or unsubstituted alkyl of 1 to 6, especially 1 to 4, carbon atoms.

$R^1$ preferably represents a group $R^a$ or —SO$_2R^a$.

Specific preferred groups which $R^1$ may represent include methyl, ethyl, n-propyl, isopropyl, n-butyl, t-butyl, n-hexyl, trichloromethyl, trifluoromethyl, chloro-t-butyl, methylsulphonyl, ethylsulphonyl, n-propylsulphonyl and isopropylsulphonyl. Particularly preferred groups are trifluoromethyl, t-butyl and isopropylsulphonyl.

Other groups which $R^1$ may represent include cyclopropyl, cyclopentyl, cyclohexyl, vinyl, allyl, propargyl, phenyl, benzyl, 2-cyanoethyl, 2-ethoxyethyl, 2-phenoxyethyl, methylthio, ethylthio, methylsulphamoyl and dimethylsulphamoyl.

X preferably represents oxygen.

R$^c$ preferably represents unsubstituted alkyl of 1 to 6, especially 1 to 4, carbon atoms.

R$^d$ preferably represents hydrogen or unsubstituted alkyl of 1 to 6, especially 1 to 4, carbon atoms.

A specific preferred group which Z may represent is methylamino.

Other groups which Z may represent include amino, ethylamino, n-propylamino, dimethylamino, phenylamino, benzylamino, acetylamino, methylsulphonylamino and piperidinyl.

R$^e$ preferably represents hydrogen, unsubstituted alkyl, alkoxy, alkylsulphonyl or acyl where the alkyl moiety is of 1 to 6, especially 1 to 4 carbon atoms, or amino.

R$^f$ preferably represents hydrogen or unsubstituted alkyl or acyl where the alkyl moiety is of 1 to 6, especially 1 to 4 carbon atoms.

Y preferably represents —NH$_2$ or a group —N=CHR$^e$.

Specific preferred groups which Y may represent include amino and those of formula —N=CHR$^e$ where R$^e$ represents methyl, phenyl, 4-chlorophenyl, 4-methoxyphenyl, 4-ethoxyphenyl, 4-cyanophenyl, 4-nitrophenyl, 4-dimethylaminophenyl and 3,4-dichlorophenyl.

Other groups which Y may represent include methylamino, dimethylamino, acetylamino, methylsulphonylamino and dimethylimino.

In a preferred group of compounds of formula I, $R^1$ represents trifluoromethyl, t-butyl or alkylsulphonyl of 1 to 4 carbon atoms, X represents oxygen, Y represents amino or a group —N=CHR$^e$ where R$^e$ represents methyl, phenyl, 4-chlorophenyl, 4-methoxyphenyl, 4-ethoxyphenyl, 4-cyanophenyl, 4-nitrophenyl, 4-dimethylaminophenyl or 3,4-dichlorophenyl, and Z represents methylamino.

Specific preferred compounds of the invention are those of the Examples provided hereinafter. Particular mention may be made, however, of 4-methyl-2-(5-t-butyl-1,3,4-thiadiazol-2-yl)semicarbazide and the acid addition salts thereof.

Preferred acid addition salts are those formed with mineral or organic acids, e.g. hydrohalic acids, especially hydrochloric or hydrobromic acid.

In another aspect, this invention provides a process for the preparation of a thiadiazole of formula I wherein Y represents —N=CR$^e$R$^f$ which comprises reacting a hydrazone of the formula:

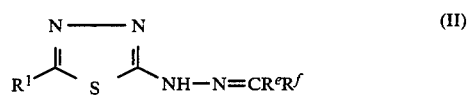

wherein $R^1$, R$^e$ and R$^f$ are as defined hereinbefore, with an isocyanate or an isothiocyanate of the formula R$^c$NCX or with a compound of the formula C$_6$H$_5$C(CN)=NOCXZ in the presence of a strong base, e.g. sodium hydride, or with a halide of the formula ZCOHal wherein Z is as defined hereinbefore and Hal represents halogen, to give the desired compound.

The reaction with the isocyanate, isothiocyanate or halide is conveniently effected in a suitable non-hydroxylic solvent medium, e.g. an ester such as ethyl acetate, a nitrile such as acetonitrile, an ether such as tetrahydrofuran or dioxane, or an amide such as dimethylformamide.

A base is desirably present which may be inorganic, e.g. sodium hydroxide, or sodium or potassium carbonate or bicarbonate, or organic, e.g. a tertiary amine, for example pyridine or triethylamine.

The reaction may proceed at room temperature, or with heating if necessary.

The hydrazones of formula II are themselves novel compounds, and this invention provides them per se.

They may be prepared by a process in which a hydrazinothiadiazole of the formula:

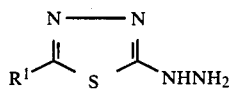

(III)

wherein $R^1$ is as defined hereinbefore, is reacted with an appropriate aldehyde or ketone of the formula $R^eCOR^f$ to give the desired compound.

The reaction is desirably effected in an appropriate solvent medium, e.g. water, or an alkanol, e.g. methanol.

The hydrazinothiadiazoles of formula III may in their turn be prepared by conventional techniques, for example reaction of hydrazine with the corresponding 2-halothiadiazoles.

The thiadiazoles of formula I wherein Y represents $-NH_2$ may be prepared by reaction of the corresponding compounds of formula I wherein Y represents $-N=CR^eR^f$ in an aqueous medium with an acid, especially a hydrohalic acid, e.g. hydrochloric or hydrobromic acid, or with hydrazine.

The thiadiazoles of formula I wherein Y represents a substituted amino group may be preparted by reaction of the compounds of formula I where Y represents $-N=CR^eR^f$ with an appropriate substituted hydrazine, or by alkylation, acylation or other conventional reaction of the compounds of formula I where Y represents $-NH_2$.

The acid addition salts of the compounds of formula I may be prepared by reaction of the corresponding free compounds with the appropriate anhydrous acid in an aprotic solvent, e.g. an ether. The unsalified compounds may be regenerated from the acid addition salts by reaction thereof with a base.

The compounds of formula I and the acid addition salts thereof are herbicidally active. In particular, they are active against wild oats (*Avena fatua*) and blackgrass (*Alopecurus myosuroides*), and broadleaf weeds. They are comparatively inactive against certain crop species, notably wheat, barley, maize and cotton, and may thus be of use as selective herbicides in crops.

In a further aspect, this invention provides a method of combating weeds at a locus infested with or liable to be infested with them, which method comprises applying to said locus a herbicidally-effective amount of one or more compounds according to the invention.

The present compounds are normally employed in the form of compositions, which can be prepared by admixing the ingredients. Usually the compositions are initially produced in the form of concentrates, e.g. containing 0.5 to 99%, especially 0.5–85% of the present compounds, and these are diluted with water or hydrocarbon, usually water, for application, generally such that the concentration of the compounds is 0.05–5%. Percentages and parts in this specification are by weight unless otherwise indicated.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

The carrier may be a liquid other than water, for example an organic solvent, such as a water immiscible solvent, e.g. a hydrocarbon which boils within the range 130°–270° C., in which the compound is dissolved or suspended. A concentrate containing a water immiscible solvent suitably also contains a surface active agent so that the concentrate acts as a self-emulsifiable oil on admixture with water. The liquid may be a water-miscible solvent e.g. 2-methoxy ethanol, methanol, propylene glycol, diethylene glycol, diethylene glycol monoethyl ether, formamide or methylformamide.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

A flowable suspension concentrate may be formed by grinding the compound with water, a wetting agent and a suspending agent.

Thus the present composition can for example be solid (e.g. dust or granules) and contain a solid carrier or liquid (e.g. an emulsifiable concentrate) and contain a liquid carrier which is a hydrocarbon which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters or phosphoric acid with a fatty alcohol ethoxylate or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise nonionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylenme oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The present active compounds and especially those specifically described herein may be admixed with another pesticide, e.g. herbicide, insecticide or fungicide, or with a plant growth regulant or with a fertilizer. Particular advantages are obtained with mixtures with a second herbicide. The present compounds may be used sequentially with a second herbicide, e.g. one herbicide applied before planting or before emergence of a crop and the other herbicide applied after emergence of the crop.

The second herbicide employed in admixture or sequentially with the compounds of the present invention may be, for example, a substituted benzofuran herbicide, a phenoxyaliphatic acid, substituted urea, triazine, phenol, nitrile, bipyridylium compound, substituted benzoic acid, halogenated aliphatic acid, carbamate, thiocarbamate, chloroacetamide, diazine, arsenic compound or other herbicidal compound. In respect of selective herbicidal compositions for post-emergence use, the second herbicide is preferably a substituted phenoxyaliphatic acid; in respect of selective herbicidal compositions for pre-emergence use, the second herbicide is preferably a substituted benzofuran, a substituted urea or triazine.

The substituted benzofuran herbicide is preferably a compound of the formula:

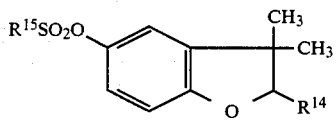

where $R^{14}$ represents hydrogen or alkoxy (especially ethoxy, propoxy or isopropoxy), and $R^{15}$ represents alkyl (especially methyl or ethyl).

A particularly preferred substituted benzofuranyl compound for admixture with the compounds of the present invention, especially with those specifically identified herein, is 2-ethoxy-2,3-dihydro-3,3-dimethylbenzofuran-5-yl methanesulphonate (common name ethofumesate).

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity.

The substituted urea generally comprises a tri- or tetra-substituted urea.

The triazine herbicide generally comprises a compound of the formula:

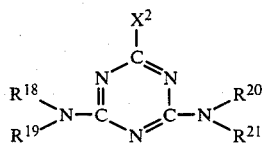

where $X^2$ is a halogen, $OY^1$ group or $SY^1$ group, where $Y^1$ is an alkyl group, and $R^{18}$, $R^{19}$, $R^{20}$ and $R^{21}$ are hydrogen or alkyl.

Specific preferred admixtures are those of one or more of the compounds specifically described herein with one or more of atrazine, ametryne, alachlor, barban, benzoylprop-ethyl, chlortoluron, chlorsulfuron, cyanazine, 2,4-D, dicamba, difenzoquat, flamprop-methyl, diclofop-methyl, isoproturon, linuron, metolachlor, metoxuron, simazine, triallate or tribunil.

The invention also provides a two-container pack in which one or more compounds of the invention are provided in a first container and one or more further pesticides, plant growth regulants or fertilizers are provided in a second container, especially in relative proportions as described hereinafter. Desirably, the two-container pack bears or contains instructions, either separate or in conjunction with one of the containers, for mixing the contents of the containers or separately applying the contents thereof.

The ratio of the present compound to the second pesticide may vary over a wide range according to the particular compounds involved and the intended use. In general the ratio of present compound to second pesticide lies in the range 1:99 to 99:1, preferably 1:0.1 to 1:15, more preferably 1:0.2 to 5:1, and especially 1:0.3 to 3:1.

The present compounds may be in admixture with non-phytotoxic oils, e.g. Agri-Oil Plus or Sun Oil 11E.

The present compounds are usually employed at a rate of from 0.5 to 8 kg per hectare, for example 1 to 4 kg per hectare.

The present compounds may be applied to plants, the soil, land or aquatic areas, and especially to a locus at which a crop is growing or is to grow. The compounds may be applied pre- or post-emergence of the crop.

The invention is illustrated by the following examples.

EXAMPLE 1

Benzaldehyde 4-methyl-2-(5-t-butyl-1,3,4-thiadiazol-2-yl)semicarbazone (a) 2-Bromo-5-t-butyl-1,3,4-thiadiazole 48% Aqueous hydrobromic acid (67.5 ml) was added to a solution of 2-amino-5-t-butyl-1,3,4-thiadiazole (43 g) in glacial acetic acid (300 ml) the mixture was warmed to 65° C. and a solution of sodium nitrite (56 g) in water (80 ml) was added dropwise with stirring over 60 minutes at 65°–75° C. The mixture was cooled to 20° C. and was poured into water. The organic layer was extracted into ether (2×300 ml) and the extracts were combined, washed with sodium bicarbonate solution until neutral and dried over magnesium sulphate. The drying agent was filtered off and the solvent was evaporated to give a yellow oil which was distilled under reduced pressure to give 2-bromo-5-t-butyl-1,3,4-thiadiazole (47 g, 78%) as a colourless liquid, bp 134°–136° C. at 23 mm Hg.

(b) 2-Hydrazino-5-t-butyl-1,3,4-thiadiazole

Hydrazine hydrate (12.5 g) was added to a solution of 2-bromo-5-t-butyl-1,3,4-thiadiazole (22.1 g) in ethanol (100 ml), and the mixture was heated under reflux for 2 hours. The solvent was evaporated to give an oily solid which was crystallised from water to give 2-hydrazino-5-t-butyl-1,3,4-thiadiazole (13.7 g, 79%) as white needles, mp 111°–112° C.

(c) Benzaldehyde 5-t-butyl-1,3,4-thiadiazol-2-ylhydrazone

A solution of benzaldehyde (5.3 g) in methanol (25 ml) was added to a solution of 2-hydrazino-5-t-butyl-1,3,4-thiadiazole (8.5 g) in methanol (40 ml). The mixture was stirred for 30 minutes, poured into water (100 ml) and filtered. The solid was crystallised from ethanol to give benzaldehyde 5-t-butyl-1,3,4-thiadiazolyl hydrazone (8.2 g, 63%) as a white powder, mp 195°–196° C.

(d) Benzaldehyde 4-methyl-2-(5-t-butyl-1,3,4-thiadiazol-2-yl)semicarbazone

Methyl isocyanate (1.88 g) was added to a stirred suspension of benzaldehyde 5-t-butyl-1,3,4-thiadiazolyl hydrazone (7.8 g) in ethyl acetate (60 ml). Triethylamine (3 drops) was then added and the mixture was stirred for 2 hours. The solvent was evaporated to give a white solid, purified by chromatography. The pure fractions were combined and recrystallised from a mixture of ethyl acetate and hexane to give benzaldehyde 4-methyl-2-(5-t-butyl-1,3,4-thiadiazol-2-yl)semicarbazone (2.1 g, 22%) as a white powder, mp 115°–116° C.

EXAMPLES 2–9

By methods analogous to that of Example 1, the following compounds of formula I were prepared where X is oxygen and Z is methylamino:

| Ex No | $R^1$ | Y | mp |
|---|---|---|---|
| 2 | t-bu | 4-chlorobenzylideneamino | 121–122° C. |
| 3 | t-bu | 4-methoxybenzylideneamino | 105–106° C. |
| 4 | t-bu | 4-cyanobenzylideneamino | 148–150° C. |
| 5 | t-bu | 4-nitrobenzylideneamino | decomp |
| 6 | t-bu | 3,4-dichlorobenzylideneamino | 143–144° C. |
| 7 | t-bu | 4-dimethylaminobenzylideneamino | 136–137° C. |
| 8 | $CF_3$ | benzylideneamino | 90–91° C. |
| 9 | t-bu | 4-ethoxybenzylideneamino | 116–117° C. |

EXAMPLE 10

Acetaldehyde 4-methyl-2-(5-t-butyl-1,3,4-thiadiazol-2-yl)semicarbazone

Sodium hydride (0.12 g) was added to a stirred solution of acetaldehyde 5-t-butyl-1,3,4-thiadiazolyl hydrazone (0.99 g) in dry toluene (25 ml), and the mixture was stirred at room temperature for 15 minutes. 2-Methylaminocarbonyloxyimino-2-phenylacetonitrile (1.01 g) was added and the mixture was stirred for a further 2 hours and poured into water (20 ml). The organic phase was separated and dried over magnesium sulphate. The drying agent was filtered off and the toluene evaporated to give a yellow oil, purified by chromatography to give acetaldehyde 4-methyl-2-(5-t-butyl-1,3,4-thiadiazol-2-yl)semicarbazone (0.6 g, 47%) as a pale yellow oil.

EXAMPLES 11–12

The following compounds were prepared by methods analogous to that of Example 10:

11. Acetone 4-methyl-2-(5-trifluoromethyl-1,3,4-thiadiazol-2-yl)semicarbazone, m.p. 89°–90° C.

12. Acetaldehyde 4-methyl-2-(5-trifluoromethyl-1,3,4-thiadiazol-2-yl)semicarbazone, m.p. 68°–69° C.

EXAMPLE 13

4-methyl-2-(5-trifluoromethyl-1,3,4-thiadiazol-2-yl)semicarbazide

Concentrated hydrochloric acid (1.0 ml) was added to a stirred suspension of acetaldehyde 4-methyl-2-(5-trifluoromethyl-1,3,4-thiadiazol-2-yl)semicarbazone in water (200 ml). The mixture was stirred at room temperature for 3 days, and was filtered. The solid was dried and crystallised from ethyl acetate to give 4-methyl-2-(5-trifluoromethyl-1,3,4-thiadiazol-2-yl)semicarbazide (10.0 g) as a white solid, mp 181°–182° C.

EXAMPLES 14–15

By a method analogous to that of Example 14 the following compounds were prepared:

14. 4-methyl-2-(5-t-butyl-1,3,4-thiadiazol-2-yl)semicarbazide, m.p. 137°–138° C.

15. 4-n-propyl-2-(5-trifluoromethyl-1,3,4-thiadiazol-2-yl)semicarbazide, mp 205°–106° C.

EXAMPLE 16

4-methyl-2-(5-ethylsulphonyl-1,3,4-thiadiazol-2-yl)semicarbazide 2,5-bis(ethanesulphonyl)-1,3,4-thiadiazole (67.5 g) was added portionwise to a stirred solution of hydrazine hydrate (25.8 g) in methanol (1000 ml) at room temperature. The mixture was then stirred for 20 minutes and filtered. The solid was crystallised from methanol to give 2-hydrazino-5-ethylsulphonyl-1,3,4-thiadiazole (16.5 g, mp 166°–167° C.). The corresponding semicarbazone was prepared from this compound by reaction with acetaldehyde, then with methylisocyanate by methods analogous to those of Example 1(c) and 1(d), and the title compound was generated by the method of Example 13, mp 151°–153° C.

EXAMPLES 17–19

By methods analogous to that of Example 16 the following compounds of formula I were prepared:

| Ex No | $R^1$ | Z | Y | X | m.p. |
|---|---|---|---|---|---|
| 17 | $CH_3SO_2$— | —$NHCH_3$ | —$NH_2$ | =O | 197–198° C. |
| 18 | n-$C_3H_7SO_2$— | —$NHCH_3$ | —$NH_2$ | =O | 170–171° C. |
| 19 | i-$C_3H_7SO_2$— | —$NHCH_3$ | —$NH_2$ | =O | 187–188° C. |

EXAMPLE 20

4-Methyl-2-(5-t-butyl-1,3,4-thiadiazol-2-yl)semicarbazide

Methyl isocyanate (14.25 g) was added dropwise over 5 minutes to a stirred suspension of acetaldehyde 5-t-butyl-1,3,4-thiadiazolyl hydrazone (49.5 g) plus potassium carbonate (8.0 g) in acetonitrile (300 ml) at room temperature. The mixture was stirred for 20 minutes and filtered, the filtrate being evaporated to give an orange oil (64 g) which contained 80% acetaldehyde 4-methyl-2b-(5-t-butyl-1,3,4-thiadiazol-2-yl)-semicarbazone.

The crude product was stirred under reflux in ethanol (300 ml) with hydrazine hydrate (12.5 g) for two hours. The solvent was evaporated to give an oily solid, treated with water (150 mls) and filtered. The solid was washed with water and dried. Crystallisation from ethyl acetate/hexane gave 4-methyl-2-(5-t-butyl-1,3,4-thiadiazol-2-yl)semicarbazide (32 g, mp 141°–142° C.).

EXAMPLE A

The compounds listed below formulated as attaclay/sand dusts were incorporated in John Innes I potting compost at a rate equivalent to 26 mg of active ingredient per liter of compost and placed in anodised aluminium pans, 19 cm long × 9.5 cm wide × 5.0 cm deep. This rate is equivalent to a soil surface application of 11.2 kg active ingredient per hectare cultivated to a depth of 5 cm. Seeds of the plant species listed below were sown in the treated compost, watered and placed in a controlled environment room (22° C.: 65-86% relative humidity: 14 hours per day artificial illumination, at 13,000 lux) for 21 days. The plants were then visually assessed for any herbicidal or growth regulant effects. All differences from an untreated control were scored according to an index where 0 = no effect and 100 = complete kill. The results are shown in the following table:

| | Compound (Ex No) | | | | | | | | |
|---|---|---|---|---|---|---|---|---|---|
| | 1 | 2 | 3 | 4 | 5 | 6 | 7 | 8 | 10 |
| | Rate. (mg/liter) | | | | | | | | |
| Species | 26 | 26 | 26 | 26 | 26 | 26 | 26 | 26 | 26 |
| Peas (*Pisum sativum*) | 70 | 80 | 78 | 72 | 60 | 30 | 68 | 70 | 80 |
| Mustard (*Sinapis alba*) | 100 | 100 | 100 | 100 | 100 | 100 | 100 | 100 | 100 |
| Linseed (*Linum usitatissimum*) | 100 | 100 | 100 | 100 | 100 | 90 | 100 | 100 | 100 |
| Ryegrass (*Lolium perenne*) | 100 | 100 | 100 | 90 | 100 | 76 | 100 | 92 | 100 |
| Oats (*Avena sativa*) | 100 | 100 | 100 | 100 | 92 | 48 | 100 | 100 | 100 |
| Maize (*Zea mays*) | 68 | 70 | 78 | 82 | 60 | 0 | 80 | 70 | 92 |

EXAMPLE B

Seeds of the plant species listed below were sown in anodised aluminum pans, 19 cm long × 9.5 cm wide × 5 cm deep, containing John Innes I potting compost. They were then watered and placed in a controlled environment room (22° C.: 65-85% relative humidity: 14 hours per day artificial illumination, at 13,000 lux). Fourteen days after sowing, the seedlings received a foliar spray of the compounds listed below, formulated as a solution in 1:1 by volume aqueous acetone.

The concentration of the test compounds and volume of application were adjusted so as to be equivalent to a rate of 2.8 kg of the compound in 450 liters per hectare. After 14 days growth in the controlled environment room, the plants were visually assessed for any herbicidal or growth regulant response. All differences from an untreated control were scored according to an index where 0 = no effect and 100 = complete kill. The results are shown in the following table:

| | Compound (Ex No) | | | |
|---|---|---|---|---|
| | 1 | 3 | 7 | 10 |
| | Rate in kg/ha | | | |
| Species | 2.8 | 2.8 | 2.8 | 2.8 |
| Peas (*Pisum sativum*) | 5 | 20 | 34 | 70 |
| Mustard (*Sinapis alba*) | 100 | 100 | 100 | 100 |
| Linseed (*Linum usitatissimum*) | 32 | 34 | 48 | 100 |
| Ryegrass (*Lolium perenne*) | 5 | 20 | 20 | 92 |
| Oats (*Avena sativa*) | 20 | 5 | 5 | 70 |
| Sugarbeet (*Beta vulgaris*) | 45 | 100 | 100 | 100 |

EXAMPLE C

Seeds of the weed species listed below were sown in anodised aluminium pans 19 cm long × 9.5 cm wide × 5 cm deep, containing sterilized sandy loam. They were watered and then sprayed with the compounds listed below formulated as an aqueous suspension together with 2 g of the polyoxyethylene (20 mols) monolaurate wetting agent per liter.

The concentration of each test compound and volume of application were calculated to give the desired rate of application of the compound in 450 liters per hectare. After four weeks growth in the controlled environment room (22° C.: 65-85% relative humidity; 14 hours per day artificial illumination at 13,000 lux) the plants were visually assessed for any herbicidal response.

All differences from an untreated control were scored according to an index where 0 = no effect, 1 = very slight effect, 2 = slight effect, 3 = moderate effect, 4 = severe effect and 5 = complete kill. The results obtained were as follows:

| | Compound (Example No.) | | | | | |
|---|---|---|---|---|---|---|
| | 13 | 14 | 16 | 17 | 18 | 19 |
| | Rate in kg/ha | | | | | |
| | 2.5 | 2.5 | 2.5 | 2.5 | 2.5 | 2.5 |
| *Stellaria media* | 5 | 5 | 5 | 5 | 5 | 5 |
| *Abutilon theophrasti* | 5 | 5 | 5 | 5 | 5 | 5 |
| *Xanthium pungens* | 5 | 5 | 5 | 5 | 5 | 5 |
| *Alopecurus myosuroides* | 5 | 5 | 5 | 5 | 5 | 5 |
| *Avena fatua* | 5 | 5 | 5 | 5 | 5 | 5 |
| *Echinochloa crus-galli* | 5 | 5 | 5 | 5 | 5 | 5 |

EXAMPLE D

Seeds of the plant species listed below were sown in anodised aluminium pans, 19 cm long × 9.5 cm wide containing sterilised sandy loams. They were then watered and placed in a controlled environment room (22° C.; 65-85% relative humidity: 14 hours per day artificial illuminations, at 13,000 lux). Fourteen or twenty-one days after sowing (depending on the species but when most plants had 2 or 3 trueleaves) the seedlings received a foliar spray of the compounds listed below, formulated as an aqueous suspension together with 2 g of the polyoxyethylene (20 mols) monolaurate wetting agent per liter.

The concentration of each test compound was calculated to give the desired rate of application of the compound in 450 liters per hectare. After 14 days growth in the controlled environment room the plants were visually assessed for any herbicidal response.

All differences from an untreated control were scored according to an index where 0=no effect, 1=very slight effect, 2=slight effect, 3=moderate effect, 4=severe effect and 5=complete kill.

|  | Compound (Example No.) | | | | | |
|---|---|---|---|---|---|---|
|  | 13 | 14 | 16 | 17 | 18 | 19 |
|  | Rate in kg/ha | | | | | |
|  | 2.5 | 2.5 | 2.5 | 2.5 | 2.5 | 2.5 |
| Stellaria media | 5 | 5 | 5 | 5 | 5 | 5 |
| Abutilon theophrasti | 5 | 5 | 5 | 5 | 5 | 5 |
| Xanthium pungens | 5 | — | 5 | 5 | 5 | 5 |
| Alopecurus myosuroides | 5 | 5 | 5 | 5 | 5 | 5 |
| Avena fatua | 5 | 5 | 5 | 5 | 5 | 5 |
| Echinochloa crus-galli | 5 | 5 | 5 | 5 | 5 | 5 |

EXAMPLE E

A 50% wettable powder formulation was prepared by grinding together the following ingredients.

Compound of Example 13: 50%

Reax 45L (sodium lignosulphonate): 5%

China clay: 45%

Similar formulations of each of the compounds of Examples 1 and 12–19 were prepared containing 0.5, 1, 5, 10, 25, 40, 75 and 85% by weight of active ingredient.

EXAMPLE F

A 20% emulsifiable concentrate formulation was prepared by dissolving the following ingredients in Solvesso 200 (aromatic hydrocarbon mixture) to make 1 liter:

Compound of Example 12: 200 g

Toximul D: 15 g

Toximul H: 85 g (Toximul D and Toximul H are anionic/nonionic blended surfactants).

Similar formulations were prepared containing 50, 100, 200, 300 and 400 grams per liter of the compounds of Examples 1 and 12–19.

We claim:

1. The thiadiazoles of the formula:

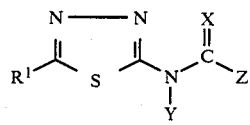

(wherein:

$R^1$ represents a group $R^a$, —S(O)n$R^a$ or —SO$_2$N-$R^a R^b$, where $R^a$ and $R^b$, which may be the same or different, each represent hydrogen, cycloalkyl of 3 to 7 carbon atoms, alkenyl or alkynyl of 2 to 6 carbon atoms, phenyl, phenylalkyl of 7 to 10 carbon atoms, or alkyl of 1 to 10 carbon atoms, any phenyl or alkyl group present being optionally substituted by one or more halogen atoms, cyano groups, alkoxy or alkylthio groups of 1 to 4 carbon atoms, or phenoxy groups, or $R^a$ and $R^b$ together form an alkylene chain of 2 to 6 carbon atoms, and n represents 0, 1 or 2;

X represents oxygen or sulphur;

Z represents a group —N$R^c R^d$; and

Y represents a group —N$R^e R^f$ or a group —N=C$R^e R^f$; where $R^c$, $R^d$, $R^e$ and $R^f$, which may be the same or different, each represent a group as defined for $R^a$, or a carboxy, alkoxy, alkoxycarbonyl, carboxylic aryl, carboxylic acyloxy alkylsulphonyl, cyano, formyl or amido, any alkyl moiety of which is of 1 to 4 carbon atoms);

and the acid addition salts thereof.

2. The thiadiazoles according to claim 1 wherein $R^a$ represents alkyl of 1 to 6 carbon atoms, optionally substituted by one or more halogen atoms.

3. The thiadiazole according to claim 1 or claim 2 wherein $R^1$ represents a group $R^a$ or —SO$_2 R^a$.

4. The thiadiazoles according to claim 1 wherein Z represents methylamino.

5. The thiadiazoles according to claim 1 wherein Y represents amino or a group —N=CH$R^e$ where $R^e$ represents methyl, phenyl, 4-chlorophenyl, 4-methoxyphenyl, 4-ethoxyphenyl, 4-cyanophenyl, 4-nitrophenyl, 4-dimethylaminophenyl or, 3,4-dichlorophenyl.

6. The thiadiazoles according to claim 2 wherein $R^1$ is selected from the group consisting of $R^a$ and —SO$_2 R^a$; Z is methylamino; Y is selected from the group consisting of amino and —N=CH$R^e$, where $R^e$ is selected from the group consisting of methyl, phenyl, 4-chlorophenyl, 4-methoxyphenyl, 4-ethoxyphenyl, 4-cyanophenyl, 4-nitrophenyl, 4-dimethylaminophenyl and 3,4-dichlorophenyl; and X represents oxygen.

7. A thiadiazole according to claim 1 which is:
4-methyl-2-(5-t-butyl-1,3,4-thiadiazol-2-yl)semicarbazide;
4-methyl-2-(5-isopropylsulphonyl-1,3,4-thiadiazol-2-yl)semicarbazide; or an acid addition salt thereof.

8. A herbicidal composition which comprises from 0.5 to 85% by weight of one or more compounds according to claim 1, in association with a suitable carrier and/or surface active agent.

9. A method of combatting weeds which comprises applying to a locus infested or liable to be infested therewith, a herbicidally effective amount of one or more compounds according to claim 1.

* * * * *